(12) United States Patent
Chaudhury et al.

(10) Patent No.: US 11,918,391 B2
(45) Date of Patent: Mar. 5, 2024

(54) ENERGY SUPPLY CIRCUIT FOR A CT SYSTEM

(71) Applicant: Siemens Healthcare GmbH, Erlangen (DE)

(72) Inventors: Shameem Kabir Chaudhury, Nuremberg (DE); Thomas Hilderscheid, Altdorf (DE); Christian Holland-Nell, Pinzberg (DE); Daniel Mueller, Dresden (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 0 days.

(21) Appl. No.: 18/064,573

(22) Filed: Dec. 12, 2022

(65) Prior Publication Data

US 2023/0181130 A1 Jun. 15, 2023

(30) Foreign Application Priority Data

Dec. 14, 2021 (DE) ...................... 10 2021 214 335.0

(51) Int. Cl.
*A61B 6/10* (2006.01)
*A61B 6/00* (2006.01)
(Continued)

(52) U.S. Cl.
CPC ................ *A61B 6/10* (2013.01); *A61B 6/035* (2013.01); *A61B 6/54* (2013.01); *A61B 6/56* (2013.01);
(Continued)

(58) Field of Classification Search
CPC .... H02J 2207/10; H02J 2310/23; H02J 50/00; H02J 50/005; H02J 50/10; H02J 50/40;
(Continued)

(56) References Cited

U.S. PATENT DOCUMENTS

| 7,634,046 B2 | 12/2009 | Krumme |
| 2017/0007197 A1 | 1/2017 | Beyerlein et al. |
| 2021/0085278 A1 | 3/2021 | Chaudhury et al. |

FOREIGN PATENT DOCUMENTS

| CN | 112535491 A | * | 3/2021 | ............ A61B 6/035 |
| DE | 102014201805 A1 | | 8/2015 | |

(Continued)

OTHER PUBLICATIONS

German Office Action and English translation thereof dated Aug. 11, 2022.
(Continued)

*Primary Examiner* — Don K Wong
(74) *Attorney, Agent, or Firm* — Harness, Dickey & Pierce, P.L.C.

(57) ABSTRACT

One or more embodiments of the present invention relates to an energy supply circuit for a CT system. The energy supply circuit comprises a stationary energy distribution device, a co-rotating bias voltage supply device, a standard energy supply path having an energy transmission device between the stationary energy distribution device and the co-rotating bias voltage supply device and an alternatively connectable service energy supply path having a voltage protection device. A computed tomography system is also described. Further, a production method for producing an energy supply circuit for a CT system is described. In addition, a method for operating a CT system is described.

13 Claims, 5 Drawing Sheets

(51) Int. Cl.
    *A61B 6/03* (2006.01)
    *H02J 1/08* (2006.01)
    *H02J 9/06* (2006.01)

(52) U.S. Cl.
    CPC .............. *H02J 1/086* (2020.01); *H02J 9/061* (2013.01); *H02J 9/068* (2020.01)

(58) Field of Classification Search
    CPC .. A61B 6/032; A61B 6/56; A61B 6/03; A61B 6/035; A61B 6/037; H05G 1/08; H05G 1/26; H05G 1/56; H05G 1/58; H05G 1/10
    See application file for complete search history.

(56) References Cited

FOREIGN PATENT DOCUMENTS

| | | |
|---|---|---|
| DE | 102014221461 A1 | 4/2016 |
| EP | 3795081 A1 | 3/2021 |

OTHER PUBLICATIONS

German Decision to Grant and English translation thereof dated Dec. 21, 2022.

\* cited by examiner

ENERGY SUPPLY CIRCUIT FOR A CT SYSTEM

CROSS-REFERENCE TO RELATED APPLICATION(S)

The present application claims priority under 35 U.S.C. § 119 to German Patent Application No. DE 10 2021 214 335.0, filed Dec. 14, 2021, the entire contents of which are incorporated herein by reference.

FIELD

One or more example embodiments of the present invention relates to an energy supply circuit for a computed tomography system. One or more example embodiments of the present invention further relates to a computed tomography system. One or more example embodiments of the present invention also relates to a method for producing an energy supply circuit for a computed tomography system. In addition, One or more example embodiments of the present invention relates to a method for operating a computed tomography system.

RELATED ART

A computed tomography system, CT system for short, requires periodic maintenance and repair. For example, it is necessary to replace the X-ray source in the scan unit of the CT system. During such a maintenance procedure it is essential to protect the engineer dealing with it against danger due to electricity. For this purpose it is necessary to separate an energy transmission unit, which comprises for example a slip ring for transmitting electrical energy from the stationary part of the scan unit of the CT system to the rotatable elements of the scan unit of the CT system, from the electricity supply network.

The new generation of photon-counting X-ray detectors uses a continuous supply via a bias voltage. If the bias voltage is interrupted, the X-ray detector requires a long time, i.e. several hours, to return to its thermal equilibrium. If the X-ray source is replaced, the X-ray detector is also decoupled from the electricity supply network in most cases. Calibration processes must therefore be carried out each time after the X-ray source is replaced. An entire working day is therefore required for replacing an X-ray source, which is time-consuming and cost-intensive.

In order to maintain the bias voltage for an X-ray detector during a maintenance procedure, a CT system comprises an additional power input, also referred to in the following as a service input, for the bias voltage supply device, which belongs to the rotating part of the scan unit, as an alternative to the slip ring. This additional power input receives electric current via a service cable. The service cable runs from a stationary energy distribution device (also referred to as a power distributor or switching or electrical cabinet) to the bias voltage supply device and supplies the detector with electric current during a maintenance procedure when the gantry or the rotating part of the scan unit is not turning. The bias voltage supply device, which, as already mentioned, co-rotates with the rotating part, has a first rectifier at its power connection or input provided for the normal operating mode. In addition, the bias voltage supply device comprises a second rectifier at its alternative power connection, also referred to as the service input, the two rectifiers together supplying an intermediate voltage.

Once the service cable for a maintenance procedure has been connected to the bias voltage supply device, the connection of the stationary energy distribution device to the electricity supply network is separated via a switch from an electrical connection to the slip ring or to the energy transmission device in general and instead is electrically connected to the service cable. As a result, the slip ring is electrically disconnected from the electricity supply network and in effect bridged, the already mentioned service input of the bias voltage supply device being connected to the electricity supply network by way of the service cable. Furthermore, in addition to the switching over of the electrical connection between the normal operating mode and the service operating mode, a supply cable is mechanically disconnected in the service operating mode from the power connection or input of the bias voltage supply device used for the normal operating mode in order to ensure that no dangerous electrical voltage is present at the slip ring in case a rectifier at the power input is defective. If, however, the supply cable is inadvertently not disconnected from the power input of the bias voltage supply device used in the normal operating mode, an engineer can receive an electric shock by touching the slip ring if a rectifier diode is defective and could possibly be seriously injured.

SUMMARY

One or more example embodiments of the present invention includes an energy supply circuit for a CT system providing increased safety for a maintenance operative, while enabling operation of the CT system to continue without delay following a maintenance operation.

Increased safety for a maintenance operative, while enabling operation of the CT system to continue without delay following a maintenance operation is achieved via the claims.

According to one or more example embodiments, an energy supply circuit for a CT system includes a stationary energy distribution device; a co-rotating bias voltage supply device; a standard energy supply path having an energy transmission device between the stationary energy distribution device and the co-rotating bias voltage supply device; and an alternatively connectable service energy supply path having a voltage protection device.

According to one or more example embodiments, the voltage protection device comprises a passive voltage protection device.

According to one or more example embodiments, the voltage protection device comprises an active voltage protection device.

According to one or more example embodiments, the voltage protection device comprises a changeover switch and an isolation transformer.

According to one or more example embodiments, the voltage protection device comprises a relay circuit having a control switch on a rotating side.

According to one or more example embodiments, the relay circuit comprises a stationary-side relay circuit.

According to one or more example embodiments, the alternatively connectable service energy supply path comprises an energy supply line; and a parallel signal transmission line to transmit a control signal of the control switch to the stationary-side relay circuit.

According to one or more example embodiments, the energy supply circuit further includes a monitoring unit configured to monitor an electrical input voltage of the bias voltage supply device in the standard energy supply path, the monitoring unit being configured to transmit a signal to the control switch to block a relay of the relay circuit in response to the monitoring unit detecting that the monitored electrical input voltage exceeds a threshold value.

According to one or more example embodiments, a computed tomography system includes a scan unit configured to acquire raw data of a patient via an X-ray detector; a control device configured to actuate the scan unit; and the energy supply circuit of claim 1, the energy supply circuit configured to provide electrical energy for the scan unit.

According to one or more example embodiments, a method for producing an energy supply circuit for a CT system includes connecting a stationary energy distribution device to a co-rotating bias voltage supply device via a standard energy supply path, the standard energy supply path having an energy transmission device between the stationary energy distribution device and the co-rotating bias voltage supply device; and setting up an alternatively connectable service energy supply path having a voltage protection device between the stationary energy distribution device and the co-rotating bias voltage supply device.

According to one or more example embodiments, a method for operating a CT system includes operating the CT system in a normal operating mode for medical imaging, the operating the CT system in the normal operating mode including, providing an energy supply for an X-ray detector of the CT system a standard energy supply path extending between a stationary energy distribution device and a co-rotating bias voltage supply device of the CT system; switching from the normal operating mode into a maintenance operating mode, the switching including, changing the energy supply for the X-ray detector via the standard energy supply path to the energy supply via a service energy supply path which comprises a voltage protection device between the stationary energy distribution device and the co-rotating bias voltage supply device; and carrying out a maintenance operation on the CT system, the CT system being protected via the voltage protection device.

According to one or more example embodiments, the method further includes a monitoring an electrical voltage in the standard energy supply path; and interrupting the service energy supply path in response to the monitored electrical voltage exceeding a predetermined threshold value.

BRIEF DESCRIPTION OF THE DRAWINGS

The invention is explained in more detail below with reference to the attached figures and with the aid of exemplary embodiments. Like components in the different figures are labeled therein with identical reference numerals.

The figures are generally not to scale. In the figures.

DETAILED DESCRIPTION

Figure 1:
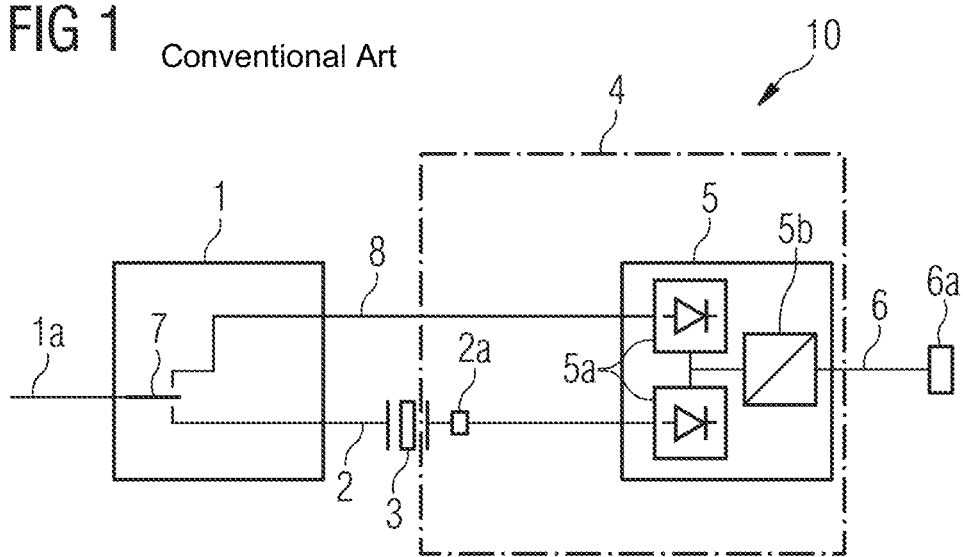
FIG. 1 schematically shows a conventional energy supply circuit of a CT system.

The inventive energy supply circuit for a CT system comprises a stationary energy distribution device. Such a stationary energy distribution device receives electric current from a stationary electricity supply network and distributes and transmits the electric current to a bias voltage supply device co-rotating with the rotating part of the scan unit of the CT system, the bias voltage supply device likewise being part of the inventive energy supply circuit. The bias voltage supply device serves to convert the electric current received from the stationary energy distribution device into direct current having a predetermined electrical bias voltage and via the electrical bias voltage to supply the X-ray detector or the modules of the X-ray detector of the CT system.

The inventive energy supply circuit also comprises a standard energy supply path having an electrical energy transmission device. Standard energy supply path is to be understood in this context as an energy transmission path for the normal operating mode of a CT system. Normal operating mode is to be understood as a mode of operation of a CT system according to specification for imaging an examination subject. The electrical energy transmission device of the standard energy supply path comprises a technical functionality for transmitting electrical energy between a stationary and a rotating part of the standard energy supply path. The energy transmission device preferably comprises a slip ring and corresponding slip ring contacts for establishing an electrical contact between the stationary energy distribution device and the co-rotating bias voltage supply device. However, it may also comprise electrically conductive coils, i.e. induction coils for contactless transmission of electrical energy.

The inventive energy supply circuit further comprises an alternatively connectable energy supply path, also referred to as a service energy supply path, between the stationary energy distribution device and the co-rotating bias voltage supply device. In contrast to conventional arrangements, the alternatively connectable energy supply path now has a voltage protection device. Thanks to the technical means of the voltage protection device in the alternatively connectable energy supply path, an engineer is protected during maintenance activities, while components of the rotating part of the scan unit of the CT system that use a constant supply of energy for technical reasons, such as, for example, the X-ray detector, in particular when the latter is a photon-counting X-ray detector, are nonetheless also supplied continuously with electrical energy during the maintenance activities, with the result that a resumption of the operation of the CT system after the maintenance procedure is possible without any time delay.

The inventive computed tomography system has a scan unit for acquiring raw data of a patient via an X-ray detector, preferably a semiconductor X-ray detector. Such a semiconductor X-ray detector is preferably embodied as a photon-counting X-ray detector. X-ray beams can be acquired in spectrally resolved form via a photon-counting X-ray detector. The inventive computed tomography system also comprises a control device for driving the scan unit and an inventive energy supply circuit for providing electrical energy for the scan unit. The inventive computed tomography system shares the advantages of the inventive energy supply circuit. In particular, the inventive computed tomography system enables a high level of safety to be achieved while at the same time providing good maintenance efficiency and low maintenance-related downtimes.

In the inventive method for producing an energy supply circuit for a CT system, a stationary energy distribution device having a co-rotating bias voltage supply device is connected via a standard energy supply path to an energy transmission device, for example a slip ring and brushes for establishing electrical contact, between the stationary energy distribution device and the co-rotating bias voltage supply device. Further, an alternatively connectable energy supply path is set up, for example at regular predetermined maintenance intervals, comprising a voltage protection device between the stationary energy distribution device and the co-rotating bias voltage supply device. Through the use of the voltage protection device, protection against electric shock is advantageously achieved for maintenance personnel during the service operating mode even in the event of a defect in the bias voltage supply device.

In the inventive method for operating a CT system, a CT system is operated in the normal operating mode for medical imaging, an energy supply for an X-ray detector of the CT system being provided via a standard energy supply path running between a stationary energy distribution device and a co-rotating bias voltage supply device of the CT system. Furthermore, when a maintenance procedure is to be carried out, a changeover is made from the normal operating mode to the maintenance operating mode, a switchover being effected from the energy supply to the X-ray detector via the standard energy supply path to the energy supply via a service energy supply path which comprises a voltage protection device between the stationary energy distribution device and the co-rotating bias voltage supply device. In the maintenance operating mode, a maintenance activity protected via the voltage protection device is carried out on the CT system. It is advantageously achieved through the use of the voltage protection device that maintenance personnel are protected against electric shock during the service operating mode even in the event of a defect in the bias voltage supply device and the power supply to the X-ray detector continues to be maintained nonetheless.

Further particularly advantageous embodiments and developments of the invention will become apparent from the dependent claims as well as from the following description, wherein the claims of one claims category may also be developed analogously to the claims and parts of the description pertaining to a different claims category and in particular individual features of different exemplary embodiments or variants may also be combined to form new exemplary embodiments or variants.

In a variant of the inventive energy supply circuit, the voltage protection device comprises a passive voltage protection device or preferably is even embodied as a passive voltage protection device. Advantageously, a voltage protection for a maintenance operative is realized independently of a functional capability of an active circuit.

In a preferred variant of the inventive energy supply circuit with passive voltage protection device, the voltage protection device comprises a changeover switch and an isolation transformer. With the aid of the changeover switch it is advantageously possible to toggle between the standard energy supply path and the alternatively connectable energy supply path, i.e. the service energy supply path, as necessary. Furthermore, the isolation transformer galvanically isolates the bias voltage supply device from the electricity supply network. Via a transformer, an electrical alternating-current voltage necessary for the service operating mode is transmitted and at the same time a galvanic isolation is created between the stationary energy distribution device and the bias voltage supply device. By this means, protection against an increased electrical voltage relative to the protective ground is achieved, in particular if the rectifier in the bias voltage supply device is defective.

In an alternative variant of the inventive energy supply circuit, the voltage protection device comprises an active voltage protection device or preferably is even embodied as an active voltage protection device. An active voltage protection device permits an emergency shutdown function to be triggered in the event of a potentially dangerous defect. A transmission of energy to the bias voltage supply device is interrupted only if a potentially dangerous defect occurs.

In a preferred embodiment of the inventive energy supply circuit with active voltage protection device, the voltage protection device comprises a switch for disconnecting the standard energy supply path from the bias voltage supply device via a switching action.

Instead of the switch, a changeover switch can also be used for switching between the standard energy supply path and the service energy supply path. The inventive energy supply circuit with active voltage protection device further comprises a preferably stationary-side relay circuit with a control switch arranged on the rotating side, preferably on the bias voltage generation device, which control switch is configured to deactivate the relay of the relay circuit as a function of a detected value of an electrical voltage present at the power supply input of the bias voltage supply device used in the normal operating mode. The supply voltage for the relay circuit can be provided by the stationary energy distribution device or alternatively by the bias voltage supply device.

In this arrangement, the relay circuit and the control switch are preferably each located at opposite end points of the service energy supply path of the inventive energy supply circuit. Deactivation is to be understood as a blocking of the relay. A blocking of a relay can be achieved for example via a spring force of an armature included in the relay via which an electrical contact is severed. An activation of the relay can be achieved via a force applied by a magnetic field which is generated by a magnetic flux that is generated by a ferromagnetic core of an exciter coil of the relay through which an electric current flows, an electrical contact being closed in the process.

A maintenance operative can advantageously be protected against an electric shock due to a defect at the power supply input used in the normal operating mode and consequently also against the electrical voltage present at the energy transmission device. This mechanism is triggered only if a defect is present, in particular a defect of the rectifier in the standard energy supply path or, as the case may be, at the power supply input of the bias voltage supply device used in the normal operating mode. Consequently, a complete interruption of the power supply to the X-ray detector is also effected only in this emergency situation. In this variant, the maintenance operative is actively protected against electric shocks due to defects. In the case of a stationary-side relay circuit, the service energy transmission path is also protected in an emergency situation against a potentially dangerous voltage by the blocking of the relay.

Preferably, the control switch is also configured to activate the relay as a function of the measured value of the electrical voltage at the power supply input used in the normal operating mode, i.e. the input in the standard energy supply path. Activation of the relay is to be understood as a switching of the relay to the conducting on-state. If, for example, the standard energy supply path is switched off, the service energy supply path can advantageously be activated automatically, thus simplifying a changeover of operating mode.

In a variant of the inventive energy supply circuit with active protection circuit, the service energy supply path comprises an energy supply line and a signal transmission line arranged in parallel, also referred to as a control line, for transmitting a control signal of the control switch to the preferably stationary-side relay. Advantageously, the alternatively connectable service energy supply path can be connected or disconnected by the bias voltage supply device. Since the danger for a maintenance operative is caused by a defect in the bias voltage supply device, a detection of the defect and an activation of the connection or disconnection by the bias voltage supply device is advantageous.

The energy supply circuit according to one or more embodiments of the present invention comprises a monitoring unit for monitoring an electrical input voltage of the bias voltage supply device in the energy transmission path used for the normal operating mode, i.e. the standard energy supply path, or at the rectifier located at the input of the bias voltage supply device to the standard energy supply path. The monitoring unit is configured to transmit a signal for blocking the relay to the already described control switch in the event that the monitoring unit detects that the monitored electrical input voltage exceeds a predetermined threshold value. In order to monitor the input voltage, the monitoring unit can comprise a voltage sensor which is arranged at the input of the bias voltage supply device in the energy transmission path used for the normal operating mode. In the event of a defect in the bias voltage supply device during a maintenance procedure, a flow of current through the service transmission path can advantageously be prevented and consequently a dangerous electrical voltage present at the bias voltage supply device or in an energy transmission path can be avoided.

In a variant of the inventive method for operating a CT system, which can be used in particular when the voltage protection device comprises an active voltage protection device, an electrical voltage in the standard energy supply path is monitored automatically in the maintenance operating mode and the service energy supply path is automatically interrupted in the event that it is detected that the monitored electrical voltage exceeds a predetermined threshold value. The threshold value can preferably comprise the value V or a negligible voltage value, for example 0.1 V, if no significant electrical voltage is to be tolerated in the standard energy supply path during a maintenance procedure. However, the threshold value can also comprise a higher voltage value specified with due regard to safety considerations.

Actual technical means for monitoring and interrupting the service energy supply path can comprise for example the already mentioned relay circuit with a control switch arranged on the rotating side of the CT system as well as the likewise mentioned monitoring unit for monitoring the electrical voltage in the standard energy supply path or at the input of the bias voltage supply device in the standard energy supply path. The power supply to the X-ray detector is advantageously maintained during the maintenance of the CT system and at the same time an exposure of a maintenance operative to danger is prevented by the automated capability of monitoring and interrupting the electricity supply.

FIG. 1 schematically shows a conventional energy supply circuit 10 of a CT system (not shown). The energy supply circuit 10 comprises a stationary energy distribution device 1, shown on the left-hand side of the image in FIG. 1, which is also referred to as a power distributor or switching or electrical cabinet, and a rotating bias voltage supply device 5, shown on the right-hand side of the image in FIG. 1, which is arranged on the rotating part 4 of the CT system, also referred to as a turntable bearing. The energy distribution device 1 comprises an electricity supply network input or power input 1a, which is shown on the left-hand side of the drawing in FIG. 1. The electricity supply network input 1a is electrically connected to a changeover switch 7, which is likewise part of the energy distribution device 1. Via the changeover switch 7 it is possible to toggle back and forth between a standard energy supply path 2 and a service energy supply path 8. The standard energy supply path 2 is used in the normal operating mode of the CT system for supplying power to the bias voltage supply device 5. A slip ring 3 of the CT system is connected to the standard energy supply path 2 as an energy transmission device which can be electrically contacted via said rotating part 4 via brushes of the rotating part 4 (see also in FIG. 7). In addition to the standard energy supply path 2, the conventional energy supply circuit 10 also comprises an alternative service energy supply path 8. The alternative service energy supply path 8 is activated as necessary, i.e. when the standard energy supply path 2 is interrupted, by operating the changeover switch 7, such that in the service operating mode an electrical connection of the electricity supply network input 1a to the co-rotating bias voltage supply device 5 is established via the alternative service energy supply path 8. The bias voltage supply device 5 has two rectifiers 5a connected in parallel, which are assigned to the two different energy supply paths 2, 8 and convert the grid electricity supplied as alternating current into direct current. The bias voltage supply device 5 further comprises a voltage converter 5b via which a suitable electrical bias voltage is generated at the bias voltage supply output 6 (shown on the right in FIG. 1) of the bias voltage supply device 5. The generated electrical bias voltage is provided to an X-ray detector 6a (represented only schematically in FIG. 1) of the CT system. In the service operating mode, before maintenance work begins, a plug 2a in the standard energy supply path 2 is also pulled in addition in order to isolate the slip ring 3, and consequently also the stationary energy distribution device 1, mechanically and electrically from the bias voltage supply device 5. In this way, if a rectifier 5a is defective, no current backflow to ground can occur if a maintenance operative inadvertently touches the slip ring 3. As already mentioned, it can happen during maintenance activities that an operative forgets to pull the plug 2a in the standard energy supply path 2, which can lead to maintenance personnel being exposed to danger if a rectifier 5a is defective.

Figure 2:
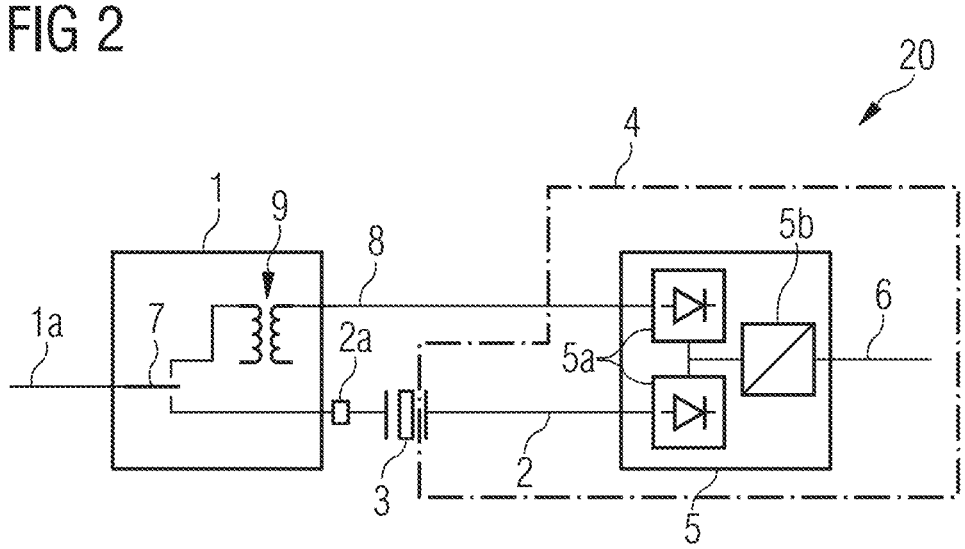
FIG. 2 shows a schematic representation of an energy supply circuit of a CT system according to a first exemplary embodiment of the invention.

FIG. 2 shows a schematic representation of an energy supply circuit 20 of a CT system according to a first exemplary embodiment of the invention. The energy supply circuit 20 shown in FIG. 2 is different from the conventional energy supply circuit 10 shown in FIG. 1 in that the alternative service energy supply path 8 comprises an isolation transformer 9. By integrating such a transformer 9 into the alternative service energy supply path 8, the service input of the bias voltage supply device 5 is not directly or not galvanically connected to the electricity supply network input 1a via the changeover switch 7 during a maintenance procedure. The isolation transformer 9 therefore galvanically separates the bias voltage supply device 5 from the electricity supply network input 1a. In this way, no dangerous electrical voltage relative to the protective ground of the standard energy supply path 2 can be transmitted to the slip ring 3 via the service energy supply path 8 in the event of a defective rectifier 5a. The energy supply circuit shown in FIG. 2 may also comprise a plug 2a not shown in FIG. 2 (see FIG. 1) which is arranged at the same point as in FIG. 1 and must be unplugged prior to upcoming maintenance activities. As already mentioned, the passive voltage protection device 9 shown in FIG. 2 forms an additional protection for a maintenance operative in this case, which protection also works if the plug 2a was inadvertently not pulled prior to the start of the maintenance activity.

Figure 3:
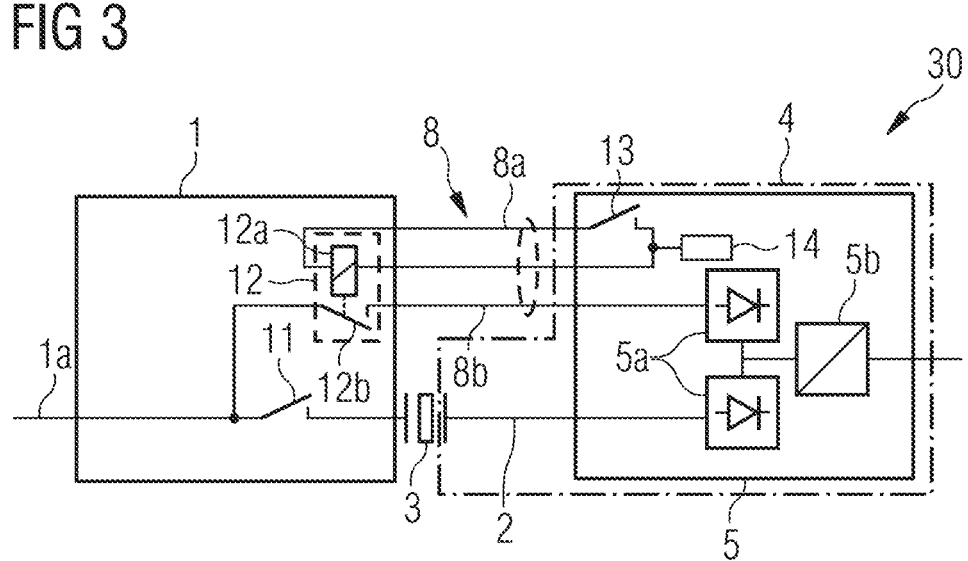
FIG. 3 shows a schematic representation of an energy supply circuit of a CT system according to a second exemplary embodiment of the invention.

FIG. 3 shows a schematic representation of an energy supply circuit 30 according to a second exemplary embodiment of the invention with active voltage protection device 12. Instead of an isolation transformer 9, the service energy supply path 8 shown in FIG. 3 comprises a relay 12 on the side of the stationary energy distribution device 1 and, on the side of the bias voltage supply device 5, a control switch 13 via which the relay 12 or a coil 12a of the relay 12 can be actuated via a control line 8a. In addition, the service energy supply path 8 also comprises an energy supply line 8b via which, when switch 12b of the relay 12 is closed, i.e. when the relay 12 is switched to the conducting on-state, energy can be transmitted in the service operating mode from the energy distribution device 1 to the bias voltage supply device 5.

Also part of the bias voltage supply device 5 is a monitoring unit 14 via which an electrical voltage at the rectifier 5a is monitored at the input of the bias voltage supply device 5 for the standard energy supply path 2. For this purpose, the monitoring unit 14 can comprise a voltage sensor and a voltage measuring unit. The voltage sensor can be arranged at the rectifier 5a, for example. When the standard energy supply path 2 is not being used for energy transmission, i.e. for example in the service operating mode, a switch 11 in the energy distribution device 1 is opened, i.e. the standard energy supply path 2 is blocked, and the monitoring unit 14 activates the relay 12 in order to connect the service energy supply path 8 or the energy supply line 8b incorporated therein electrically to the electricity supply network input 1a. If an electrical voltage is present in the service operating mode at the input of the bias voltage supply device 5 to the standard energy supply path 2, for example due to a defective rectifier 5a, the monitoring unit 14 detects said electrical voltage, for example via a measurement with a voltage sensor, and deactivates the relay 12 by operating the control switch 13. By a deactivation is meant that the relay 12 is placed into a blocking state. As a result of the deactivation of the relay 12 via the control switch 13, dangerous electrical voltages at the slip ring 3 or other components that are to undergo maintenance are avoided while the service energy supply path 8 is active. The relay 12 operates in cooperation with the control switch 13 and the monitoring unit 14 as a kind of emergency switch via which a defect in the bias voltage supply device 5 is automatically detected and in such a case the service energy supply path 8 is actively blocked. The energy supply circuit shown in FIG. 3 can also comprise a plug 2a (see FIG. 1) which is arranged at the same point as in FIG. 1 and must be pulled ahead of upcoming maintenance activities. As already mentioned, it can happen during maintenance operations that said plug 2a has mistakenly not been pulled in advance and in this case the described voltage protection device 12 automatically comes into use if a dangerous electrical voltage occurs at the bias voltage supply device 5.

Figure 4:
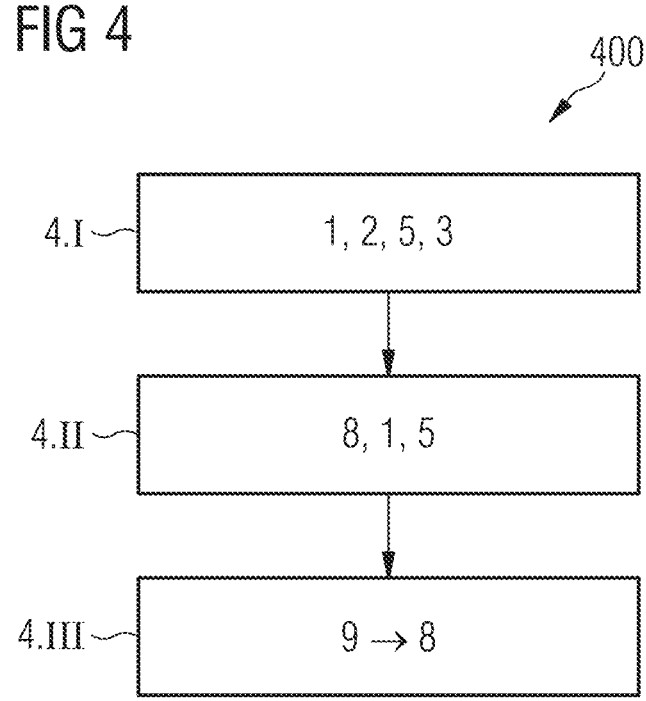
FIG. 4 shows a flowchart illustrating a production method for producing an energy supply circuit for a CT system according to a first exemplary embodiment of the invention.

FIG. 4 shows a flowchart 400 illustrating a method for producing an energy supply circuit for a CT system having a passive voltage protection device according to an exemplary embodiment of the invention. The method comprises the following steps:

At step 4.I, a stationary energy distribution device 1 is connected to a co-rotating bias voltage supply device 5 via a standard energy supply path 2. The standard energy supply path 2 comprising a slip ring 3 and corresponding brush contacts is embodied here as an electrical contact between the stationary energy distribution device 1 and the co-rotating bias voltage supply device 5.

At step 4.II, an alternatively connectable service energy supply path 8 is embodied between the stationary energy distribution device 1 and the co-rotating bias voltage supply device 5.

At step 4.III, an isolation transformer 9 is embodied in the alternatively connectable service energy supply path 8 between the stationary energy distribution device 1 and the co-rotating bias voltage supply device 5.

Figure 5:
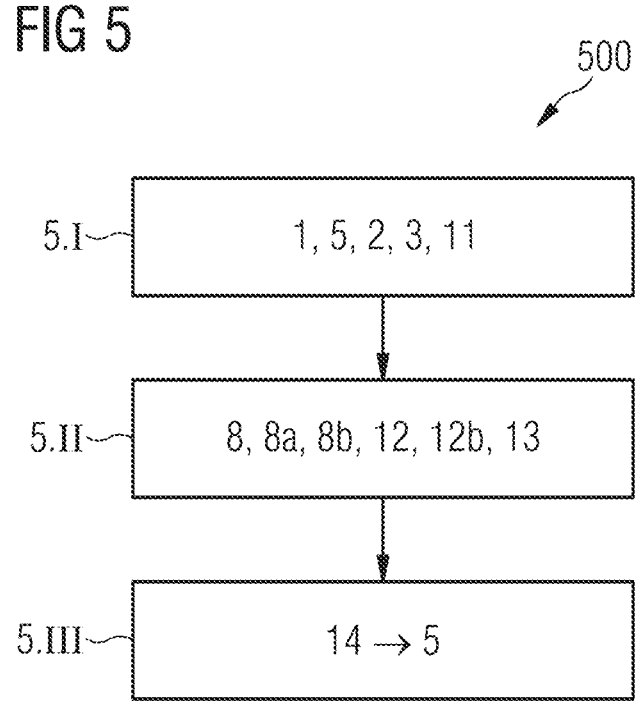
FIG. 5 shows a flowchart illustrating a production method for producing an energy supply circuit for a CT system according to a second exemplary embodiment of the invention.

FIG. 5 shows a flowchart 500 illustrating an alternative method for producing an energy supply circuit for a CT system having an active voltage protection device according to an exemplary embodiment of the invention. The method comprises the following steps:

At step 5.I, a stationary energy distribution device 1 is electrically connected to a bias voltage supply device 5 co-rotating with the rotating part of the CT system via a standard energy supply path 2. The standard energy supply path 2 is embodied in this case with a slip ring 3 as the electrical contact between the stationary energy distribution device 1 and the co-rotating bias voltage supply device 5. In the standard energy supply path 2, an electrical switch 11 via which the connection of the stationary energy distribution device 1 to the standard energy supply path 2 can be interrupted prior to the start of the service operating mode is embodied on the stationary side.

At step 5.II, an alternatively connectable service energy supply path 8 is embodied between the stationary energy distribution device 1 and the co-rotating bias voltage supply device 5. In this case, a control path and an energy transmission path are embodied with a control line 8a and an energy supply line 8b, respectively. On the side of the energy distribution device 1, a relay 12 is integrated into the service energy supply path 8 instead of an isolation transformer 9, and on the side of the bias voltage supply device 5, a control switch 13 is integrated into the service energy supply path 8, which control switch 13 is configured to actuate the relay 12 or energize a coil 12a of the relay 12 via the control line 8a.

When switch 12b of the relay 12 is closed, energy can be transmitted in this way in the service operating mode from the energy distribution device 1 to the bias voltage supply device 5.

At step 5.III, a monitoring unit 14 is also integrated into the bias voltage supply device 5 to enable the electrical voltage at a rectifier 5a at the input of the bias voltage supply device 5 for the standard energy supply path 2 to be monitored. If an electrical voltage is detected by the monitoring unit 14 in the service operating mode at the input of the bias voltage supply device 5 for the standard energy supply path 2, the relay 12 is deactivated via the control switch 13 as a precaution so that no current can flow via the service energy supply path 8.

Figure 6:
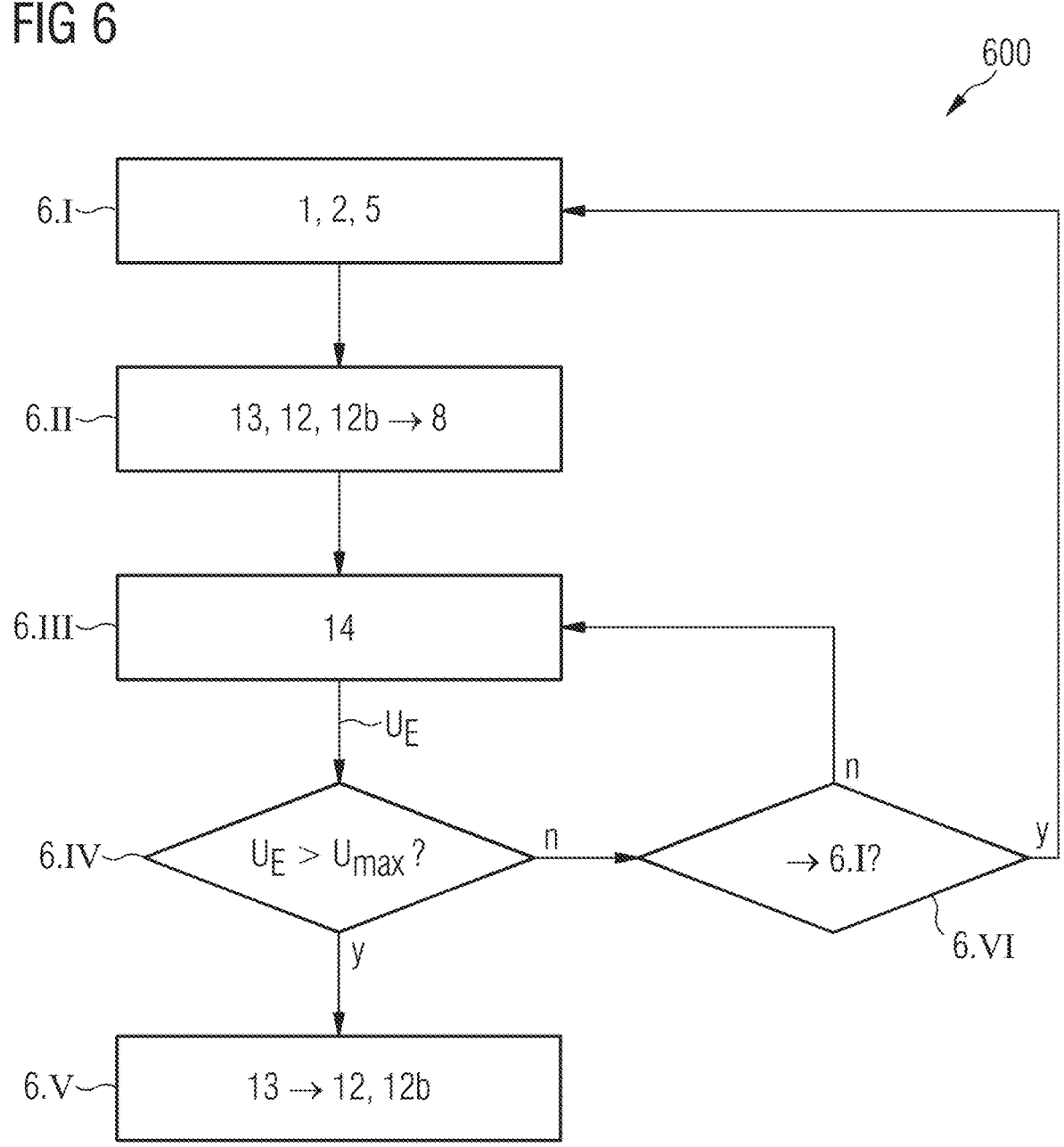
FIG. 6 shows a flowchart illustrating a method for operating an energy supply circuit for a CT system according to an exemplary embodiment of the invention.

FIG. 6 shows a flowchart 600 illustrating a method for safely operating a CT system according to one or more embodiments of the present invention. The method comprises the following steps:

At step 6.I, a CT system is used for medical imaging in the normal operating mode. In this mode, the X-ray detector is supplied with electrical energy from the electricity supply network by way of an energy distribution device 1, a standard energy supply path 2 and a bias voltage supply device 5.

At step 6.II, a switch is made from the normal operating mode into the maintenance or service operating mode. To that end, the standard energy supply path 2 is interrupted by the opening of an electrical switch 11. In addition, a relay 12 is actuated via a control switch 13 such that the coil of the relay is activated and closes the switch 12b of the relay 12 or switches it to the conducting on-state. The X-ray detector is now supplied with electrical energy via the service energy supply path 8.

At step 6.III, the electrical voltage UE at the input of the bias voltage supply device 5 to the standard energy supply path 2 is monitored during the service operating mode via a monitoring unit 14.

At step 6.IV, it is determined via the monitoring unit 14 whether the electrical voltage UE at the input of the bias voltage supply device 5, which input is electrically connected to the standard energy supply path 2, exceeds a predetermined threshold value Umax.

In the event that it is detected that the input voltage UE exceeds the predetermined value Umax, as indicated by "y" in FIG. 6, a transition is made to step 6.V. In the event that the predetermined value Umax is not exceeded, as indicated by "n" in FIG. 6, a return is made to step 6.VI.

At step 6.V, a control switch 13 is activated, which in turn causes the relay 12 to open the switch 12b such that the service energy supply path 8 is interrupted and prevents a potentially dangerous electrical voltage UE from continuing to be applied at the input of the bias voltage supply device 5.

At step 6.VI, it is determined whether a transition is to be made into the normal operating mode, i.e. to step 6.I. If this question is answered in the affirmative, as indicated by "y" in FIG. 6, a transition is made to step 6.I. Otherwise, as indicated by "n" in FIG. 6, a return is made to step 6.III and the input voltage UE continues to be monitored in the service operating mode.

Figure 7:
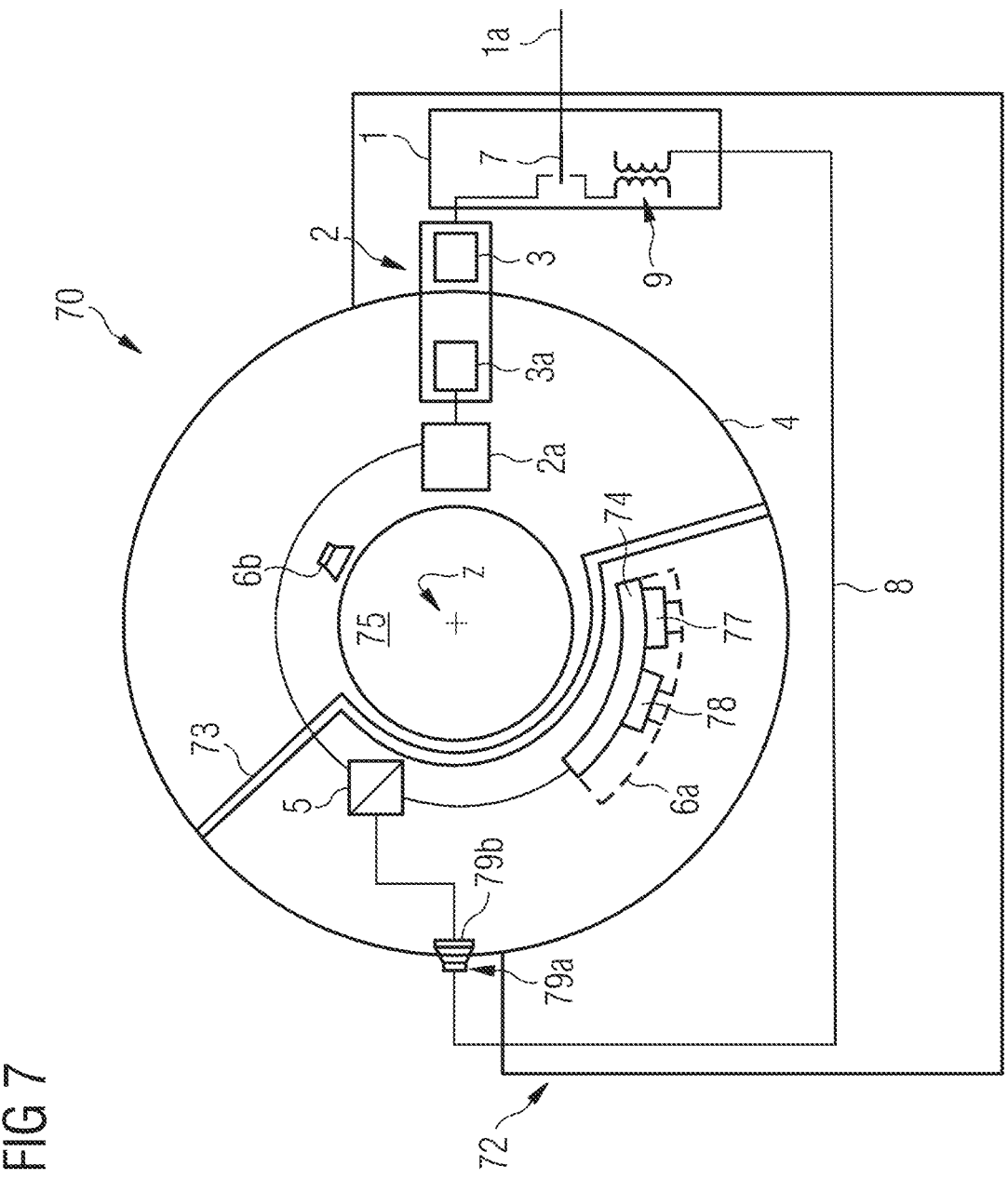
FIG. 7 shows a schematic representation of a CT system according to an exemplary embodiment of the invention.

FIG. 7 schematically shows a cross-sectional view of a CT system 70 according to an exemplary embodiment of the invention. In this case the CT system 70 comprises a turntable bearing 4 as the moving part and a mounting frame 72 as the static part. In this arrangement, the turntable bearing 4 is rotatably mounted relative to the mounting frame 72 around an axis z standing perpendicularly to the image plane in the center of the turntable bearing 4. An X-ray detector 6a is arranged on the turntable bearing 4 in an electrical isolation means 73. The bias voltage supply device 5 is connected to a standard energy supply path 2 which includes an energy-consuming component 3a that is in electrical contact with a stationary energy distribution device 1. The standard energy supply path 2 also comprises the plug 2a already shown in FIG. 1, via which the standard energy supply path 2 can be interrupted if necessary.

An energy-supplying component 3 of the standard energy supply path 2 arranged on the mounting frame 72 is connected to a power source, which can be provided via a connection to the electricity supply grid or by the already mentioned stationary energy distribution device 1. The power source 1, the standard energy supply path 2 and the bias voltage supply device 5, together with the corresponding connection lines, form the essential components of a first power supply. In this arrangement, the energy-consuming component 3a and the energy-supplying component 3 can each be embodied as coils of a coil pair for inductive energy transmission or as a slip ring 3 having a slip ring contact 3a.

The X-ray detector 6a has a layer of a semiconductor material 74 which is attached in such a way that an X-ray (not shown in further detail) generated by an X-ray source 6b (and possibly partially scattered and/or absorbed by an object positioned in the interior 75 of the turntable bearing 4) impinges on the semiconductor material 74. The semiconductor material may in this case be composed in particular of cadmium telluride or cadmium zinc telluride, or else by a comparable semiconductor having similar relevant properties.

The semiconductor material 74 is interconnected with a bias voltage supply device 5 in such a way that a bias voltage can be applied to the semiconductor material 74 by the bias voltage supply device 5. Further, the semiconductor material 74 is thermally coupled to a heating element 77 and a cooling element 78. The heating element 77 is configured to heat the semiconductor material 74 in order to increase the mobility of free charge carriers there. This facilitates a saturation of the impurity traps in the semiconductor material 74 on the one hand, and on the other hand increases the linearity for free charge carriers generated in the semiconductor material 74 by X-rays emitted by the X-ray source 6b. The cooling element 78 is configured to reduce the temperature of the semiconductor material 74 if said temperature assumes a critical value as a result of incident X-rays.

The heating element 77 and the cooling element 78 are connected to a regulator device (not shown) which is configured to regulate the temperature of the semiconductor material 74 and in the process enables the mobility of free charge carriers to be increased further, in particular by heating, when the power supply via the standard energy supply path 2 is disconnected. For this purpose, the regulator device is connected to a temperature sensor (not shown in further detail) which measures a temperature of the semiconductor material 74.

For the idle mode, also referred to in the foregoing as the service operating mode, in which the power supply via the standard energy supply path 2 is disconnected, while in addition, for safety reasons, the plug 2a disposed in said standard energy supply path 2 is pulled, the CT system has a service energy supply path 8 which is connected to the X-ray detector 6a via the bias voltage supply device 5, which comprises a rectifier 5a (shown in FIG. 2) and a voltage converter 5b.

The service energy supply path 8 comprises an energy-consuming component 79b arranged on the turntable bearing 4 and an energy-supplying component 79a arranged at least partially on the mounting frame 72. In the present arrangement, the energy-consuming component 79b is formed by an outlet for a plug. The energy-supplying component 79a comprises a plug and a cable which forms the service energy supply path 8. The power source 1, also referred to in the foregoing as the power distributor or energy distribution device, comprises a changeover switch 7 for switching between the standard energy supply path 2 and the service energy supply path 8, an electricity supply network input 1a, and an isolation transformer 9 for galvanically separating the turntable bearing 4 from the electricity supply network in the service operating mode.

However, as an alternative to the illustrated embodiment variant, or also in addition thereto, the energy-consuming component 79b and the energy-supplying component 79a of the service energy supply path 8 may comprise a pair of induction coils for providing inductive energy transmission.

In the idle state or service operating mode, a temperature set by the heating element 77 or the cooling element 78 in the semiconductor material 74 of the X-ray detector 6a via the bias voltage of the bias voltage supply device 5 therefore continues to maintain the equilibrium of the occupation states of the impurity traps, the power now being supplied via the service energy supply path 8.

Owing to the electrical isolation means 73 and the rectifier 5a (not shown) of the bias voltage supply device 5, except for the X-ray detector 6a itself, the turntable bearing 4 is deenergized in the idle state, thus enabling maintenance or repair work that does not concern the X-ray detector 6a to be carried out during this time.

The loads arranged on the turntable bearing 4 for image generation purposes, such as, for example, the X-ray source 6b, thus form a first set of components which are supplied with power via the standard energy supply path 2 in the operating state of the CT system 70. As a result of the isolation means 73 and the separation realized within the circuitry via the rectifier 5a (not shown), the bias voltage supply device 5, the heating element 77 and the cooling element 78 form a second set of components which are supplied with power in the idle state, i.e. when the standard energy supply path 2 is disconnected, via the service energy supply path 8 in order to maintain the semiconductor material 74 of the X-ray detector 6a as far as possible in an operable state.

The semiconductor material 74 of the X-ray detector 6a is in this case maintained in an operable state also during the normal operating state of the CT system 70 by the components of the second set, in which case, if necessary, the heating element 78 can be deactivated during a single X-ray acquisition. In the normal operating state, the components of the second set can in this case draw their power through the standard energy supply path 2 such that the electricity supply via the service energy supply path 8 takes over the power supply to the second set of components only in the idle state.

In conclusion, it is pointed out once again that the devices and methods described in detail hereinabove are simply exemplary embodiments which can be modified in the most diverse ways by the person skilled in the art without leaving the scope of the invention. Furthermore, the use of the indefinite articles "a" or "an" does not exclude the possibility that the features in question may also be present more than once. Similarly, the term "unit" does not rule out the possibility that this consists of a plurality of components which if necessary may also be distributed in space.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein and mentioned above, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

In addition, or alternative, to that discussed above, units and/or devices according to one or more example embodiments may be implemented using hardware, software, and/ or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/ hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module', 'interface' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing system or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, Cif, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium, storage means or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

The invention claimed is:

1. An energy supply circuit for a CT system, the energy supply circuit comprising:
   a stationary energy distribution device;
   a co-rotating bias voltage supply device;
   a standard energy supply path having an energy transmission device between the stationary energy distribution device and the co-rotating bias voltage supply device; and
   an alternatively connectable service energy supply path having a voltage protection device.

2. The energy supply circuit of claim 1, wherein the voltage protection device comprises a passive voltage protection device.

3. The energy supply circuit of claim 1, wherein the voltage protection device comprises an active voltage protection device.

4. The energy supply circuit of claim 2, wherein the voltage protection device comprises a changeover switch and an isolation transformer.

5. The energy supply circuit of claim 3, wherein the voltage protection device comprises a relay circuit having a control switch on a rotating side.

6. The energy supply circuit of claim 5, wherein the relay circuit comprises a stationary-side relay circuit.

7. The energy supply circuit as claimed in claim 6, wherein the alternatively connectable service energy supply path comprises:
   an energy supply line; and
   a parallel signal transmission line to transmit a control signal of the control switch to the stationary-side relay circuit.

8. The energy supply circuit of claim 6, further comprising:
   a monitoring unit configured to monitor an electrical input voltage of the bias voltage supply device in the standard energy supply path, the monitoring unit being configured to transmit a signal to the control switch to block a relay of the relay circuit in response to the monitoring unit detecting that the monitored electrical input voltage exceeds a threshold value.

9. A computed tomography system comprising:
   a scan unit configured to acquire raw data of a patient via an X-ray detector;
   a control device configured to actuate the scan unit; and
   the energy supply circuit of claim 1, the energy supply circuit configured to provide electrical energy for the scan unit.

10. A method for producing an energy supply circuit for a CT system, the method comprising:
    connecting a stationary energy distribution device to a co-rotating bias voltage supply device via a standard energy supply path, the standard energy supply path having an energy transmission device between the stationary energy distribution device and the co-rotating bias voltage supply device; and
    setting up an alternatively connectable service energy supply path having a voltage protection device between the stationary energy distribution device and the co-rotating bias voltage supply device.

11. A method for operating a CT system, the method comprising:

operating the CT system in a normal operating mode for medical imaging, the operating the CT system in the normal operating mode including,
providing an energy supply for an X-ray detector of the CT system a standard energy supply path extending between a stationary energy distribution device and a co-rotating bias voltage supply device of the CT system;
switching from the normal operating mode into a maintenance operating mode, the switching including,
changing the energy supply for the X-ray detector via the standard energy supply path to the energy supply via a service energy supply path which comprises a voltage protection device between the stationary energy distribution device and the co-rotating bias voltage supply device; and
carrying out a maintenance operation on the CT system, the CT system being protected via the voltage protection device.

12. The method as claimed of claim 11, further comprising:
monitoring an electrical voltage in the standard energy supply path; and
interrupting the service energy supply path in response to the monitored electrical voltage exceeding a predetermined threshold value.

13. The energy supply circuit of claim 7, further comprising:
a monitoring unit configured to monitor an electrical input voltage of the bias voltage supply device in the standard energy supply path, the monitoring unit being configured to transmit a signal to the control switch to block a relay of the relay circuit in response to the monitoring unit detecting that the monitored electrical input voltage exceeds a threshold value.

* * * * *